(12) United States Patent
de Guillebon et al.

(10) Patent No.: US 7,182,775 B2
(45) Date of Patent: Feb. 27, 2007

(54) SUPER ATRAUMATIC GRASPER APPARATUS

(75) Inventors: Henri de Guillebon, Manchester, MA (US); Genci Omari, Gloucester, MA (US)

(73) Assignee: Microline Pentax, Inc., Beverly, MA (US)

( * ) Notice: Subject to any disclaimer, the term of this patent is extended or adjusted under 35 U.S.C. 154(b) by 484 days.

(21) Appl. No.: 10/375,528

(22) Filed: Feb. 27, 2003

(65) Prior Publication Data

US 2004/0172057 A1 Sep. 2, 2004

(51) Int. Cl.
*A61B 17/00* (2006.01)
(52) U.S. Cl. .................................... 606/207
(58) Field of Classification Search ........ 606/205–211, 606/51–52; D24/143
See application file for complete search history.

(56) References Cited

U.S. PATENT DOCUMENTS

| | | | |
|---|---|---|---|
| 3,503,396 A * | 3/1970 | Pierie et al. ............... | 606/207 |
| 5,690,269 A * | 11/1997 | Bolanos et al. ........... | 227/176.1 |
| 5,728,121 A * | 3/1998 | Bimbo et al. ............. | 606/207 |
| 5,964,779 A * | 10/1999 | Mayenberger et al. .... | 606/205 |
| 6,228,083 B1 * | 5/2001 | Lands et al. .............. | 606/50 |
| 6,238,414 B1 * | 5/2001 | Griffiths ................... | 606/205 |
| 6,558,408 B1 * | 5/2003 | Fogarty et al. ............ | 606/207 |
| 6,579,304 B1 * | 6/2003 | Hart et al. ................. | 606/207 |
| 6,656,193 B2 * | 12/2003 | Grant et al. ............... | 606/151 |
| 2003/0191465 A1 | 10/2003 | Yahagi et al. | |

* cited by examiner

*Primary Examiner*—Anhtuan T. Nguyen
*Assistant Examiner*—Elizabeth Houston
(74) *Attorney, Agent, or Firm*—Greenblum & Bernstein, P.L.C.

(57) ABSTRACT

The present invention comprises a grasper arrangement having a pair of opposed, elongated, movable jaw members at a distal end of the grasper arrangement pinchably actuatable from a handle portion at a proximal end of the grasper arrangement. The jaw members each have a toothed insert attachably secured thereon. Each tooth insert has an array of teeth disposed thereon on a first side thereof. Each tooth insert has a securement arrangement on a second side thereof to securely engage the jaw member thereto. Each of the jaw members are of decreasing tapered thickness from a distal end thereof to a proximal end thereof.

9 Claims, 9 Drawing Sheets

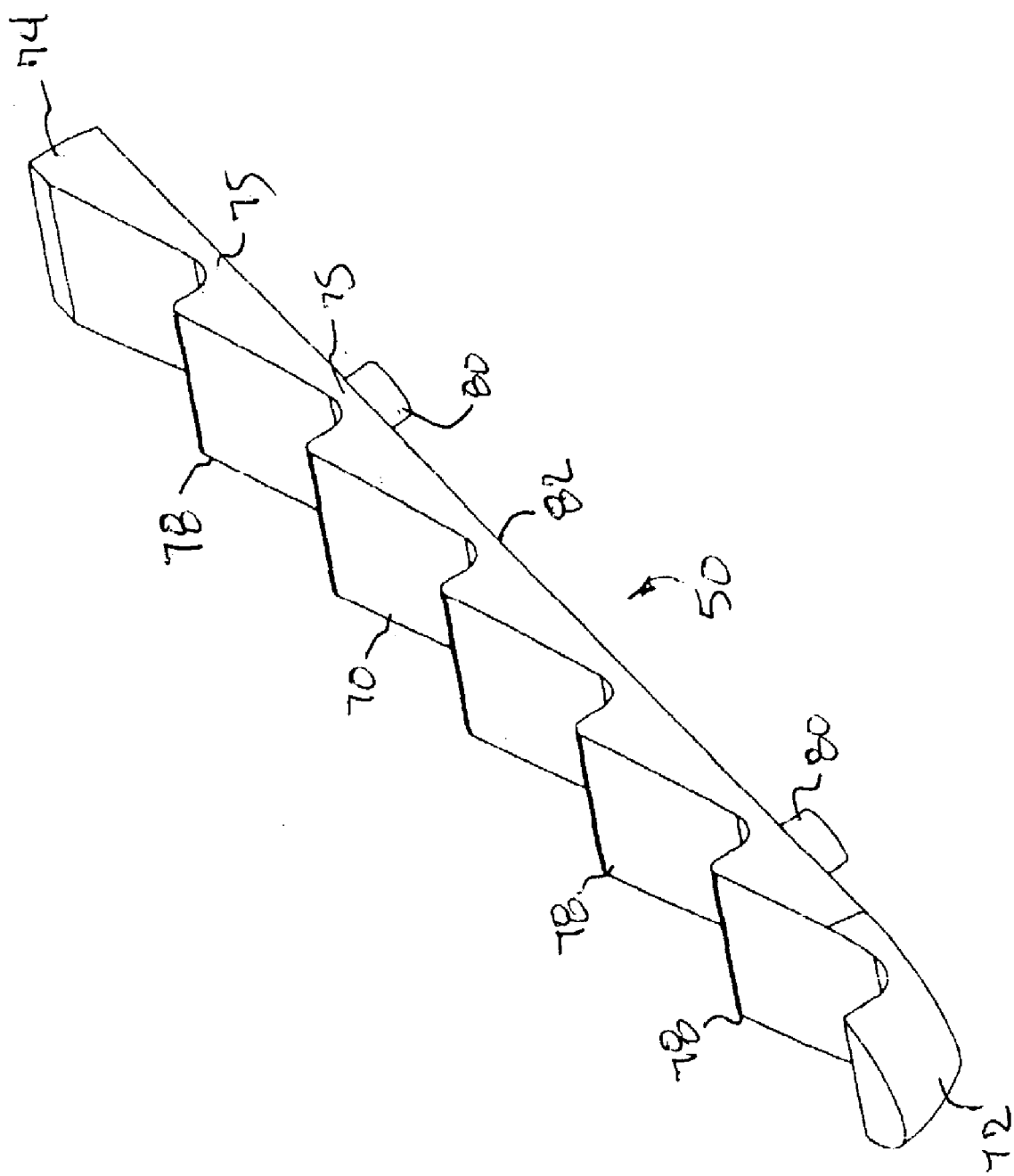

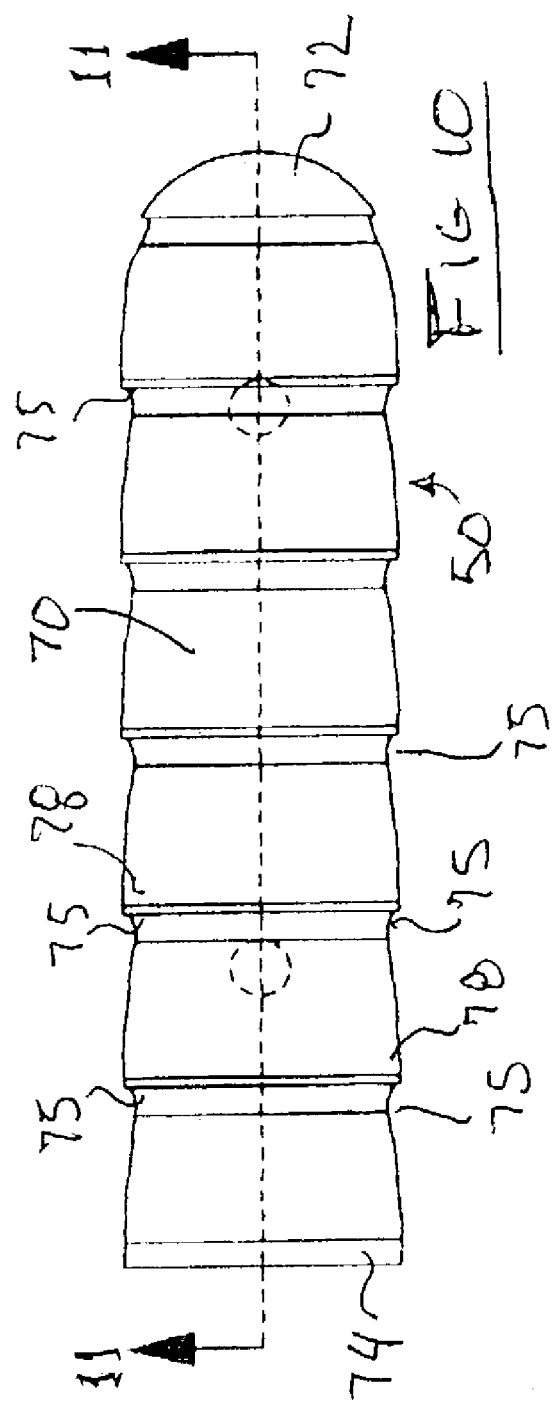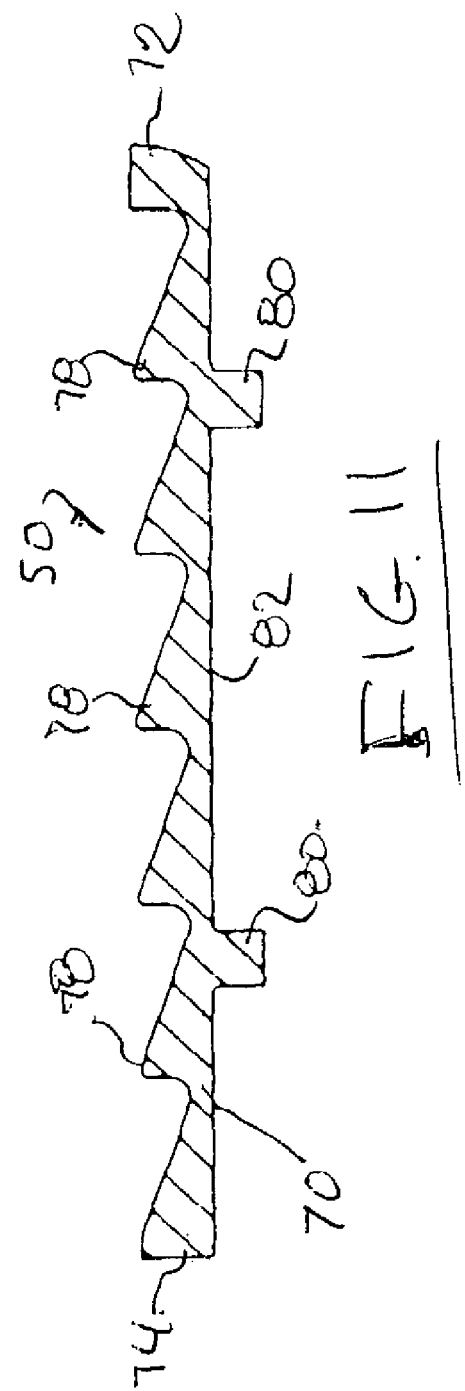

SUPER ATRAUMATIC GRASPER APPARATUS

BACKGROUND OF THE INVENTION

Field of the Invention

The present invention relates to elongated body tissue grasping devices and more particularly to a jaw assembly for such medically related grasper devices.

PRIOR ART

Advances in modern medicine have included techniques for laparoscopic surgery which permits the minimally invasive surgical techniques to be utilized on the human body. Such techniques include very small incisions so as to access tissue within that body. Thin elongated devices are inserted through those narrow slit incisions to treat and manipulate the tissue within the body.

Certain tissue within the body has to be treated a little more sensitively than other tissue, for example, gynocological tissue. Such body tissue may be torn or injured if the operating surgeon is not careful.

It is an object of the present invention to provide a grasping device for use in surgical procedures where the tissue to be grasped is not damaged by the grasping device.

It is further object of the present invention to provide improvements for grasping devices over the prior art.

It is yet still a further object of the present invention to provide a grasping device having a jaw arrangement which may be modified by the attending surgeon.

It is yet still a further object of the present invention to provide a grasping device having a jaw arrangement which is a traumatic.

It is still yet a further object of the present invention where the jaw arrangement of a grasper device has hollow portions for non-pinching receipt of tissue being grasped.

BRIEF SUMMARY OF THE INVENTION

The present invention comprises an elongated forceps arrangement or grasper for gently holding and gently manipulating tissue within the human body. The grasper arrangement comprises a first or handle end having a manipulable and squeezable trigger member which is advanceable towards a stationary frame member which actuates a pair of jaws which are located at the second or distal end of the grasper assembly. The jaws at the distal end of the grasper assembly are arranged to pivot about a pivot pin when the trigger and frame are moved with respect to one another, thus bringing the jaws into engagement or spreading them apart, accordingly.

Each jaw of the pair of jaws comprises a first end plate of planar configuration which is unitary with an elongated jaw member body. The elongated jaw member body is generally planar and has a second or distalmost end. The elongated jaw member body has a jaw face which is generally flat. The jaw face has a plurality of openings or detents therein. The first end plate has an opening for the pivot pin to extend therethrough and has an elongated slot to function as cam slot for the push-pull rod extending through the housing from the frame end at the proximal end of the grasper assembly.

Each jaw member is arranged to receive a "grasping-teeth set". Each grasping-teeth set is molded from a soft pliable material such as plastic, polyethylene, polypropylene, rubber or the like. Each grasping-teeth set may have varying hardness or durometer at its raised portions thereon.

A first embodiment of a grasping-teeth set comprises an elongated mold of resilient material which mates with the jaw face of each particular jaw member. The grasping-teeth set jaw insert in a first preferred embodiment comprises a pair of sinusoidally faced wavy teeth, spaced apart and parallel, extending along each side edge of the grasping-teeth set jaw insert. A central elongated tissue receiving channel is arranged between the respective parallel sinusoidally faced wavy teeth array of this grasping-teeth set jaw insert. The wavy faced jaw insert has a distalmost end of curved configuration, which matches the distal end of the jaw face of the elongated jaw member. The grasping-teeth set jaw insert has a proximal end of rectilinear configuration which abuts a shoulder at the proximal end of the jaw face of the elongated jaw member. The wavy faced (or sinusoidal) grasping-teeth set jaw insert has a back plane which mates against the jaw face. A tab extends perpendicular to the back plane of the jaw insert and mates within the openings within the jaw face of its respective elongated jaw member. The tabs and insert openings snap fit so as to securely mate the grasping-teeth set jaw insert against the particular elongated jaw member. Each set of waves in the wavy or sinusoidal tooth array has its crest height diminishing from distal to the proximal end of the jaw insert. This permits a superior distal grasping and gripping of tissue when it is pinched between the pairs of jaws when in use in a body tissue procedure. The elongated tissue receiving channel between the parallel array of wavy teeth in the grasping-teeth set jaw insert permits body tissue to be safely enclosed therewithin, with minimal damage thereto.

A further embodiment of the grasping-teeth set jaw insert comprises an elongated saw-tooth insert having a curved distalmost end and a rectilinear shaped proximal end. There are a series of transversely extending teeth having a "saw tooth" configuration. The height of each saw tooth as measured from a back plane of the jaw insert diminishes from the distalend to the proximal end of the jaw insert. This permits the grasping-teeth set jaw inserts when arranged in a set of elongated jaw members to be in an abutting relationship when those jaw members are closed and a slightly increasing gap between those pressed portions of the saw tooth insert in a proximal direction thereof. The saw tooth configured insert has a plurality of tabs extending perpendicular to its rear planar face. Those tabs are mateably received within the insert openings in the elongated jaw member. The inserts in a further embodiment may be secured to the jaws by adhesive, or the inserts may be "over-molded" onto the jaws for securement thereto by such overmolding.

The invention thus comprises a grasper arrangement having a pair of opposed, elongated, movable jaw members at a distal end of the grasper arrangement pinchably actuatable from a handle portion at a proximal end of the grasper arrangement. The jaw members each have a toothed insert attachably secured thereon.

Each tooth insert has an array of teeth disposed thereon from a first side thereof. Each tooth insert has a securement member on a second side thereof to securely engage the jaw member thereto. Each of the jaw members being of decreasing tapered thickness from a distal end thereof to a proximal end thereof.

The array of teeth may be of wavy sinusoidal form in cross-section. The array of teeth may be of saw tooth configuration in cross-section. The wavy form of the teeth have an elongated channel extending longitudinally of the tooth insert. The securement may comprise a tab extending off of a backside of each of the tooth inserts. Each of the jaw members may have an indentation for receipt of the tab on the tooth insert. The toothed inserts are preferably comprised of soft resilient material.

BRIEF DESCRIPTION OF THE DRAWINGS

The objects and advantages of the present invention will become more apparent when viewed in conjunction with the following drawings in which:

FIG. 9 is a perspective view of a saw tooth jaw insert constructed according to the principles of the present invention;

FIG. 10 is a planned view of the jaw insert shown in FIG. 9; and

FIG. 11 is a view taken along the lines 11—11 in FIG. 10.

DETAILED DESCRIPTION OF THE PREFERRED EMBODIMENTS

Figure 1:
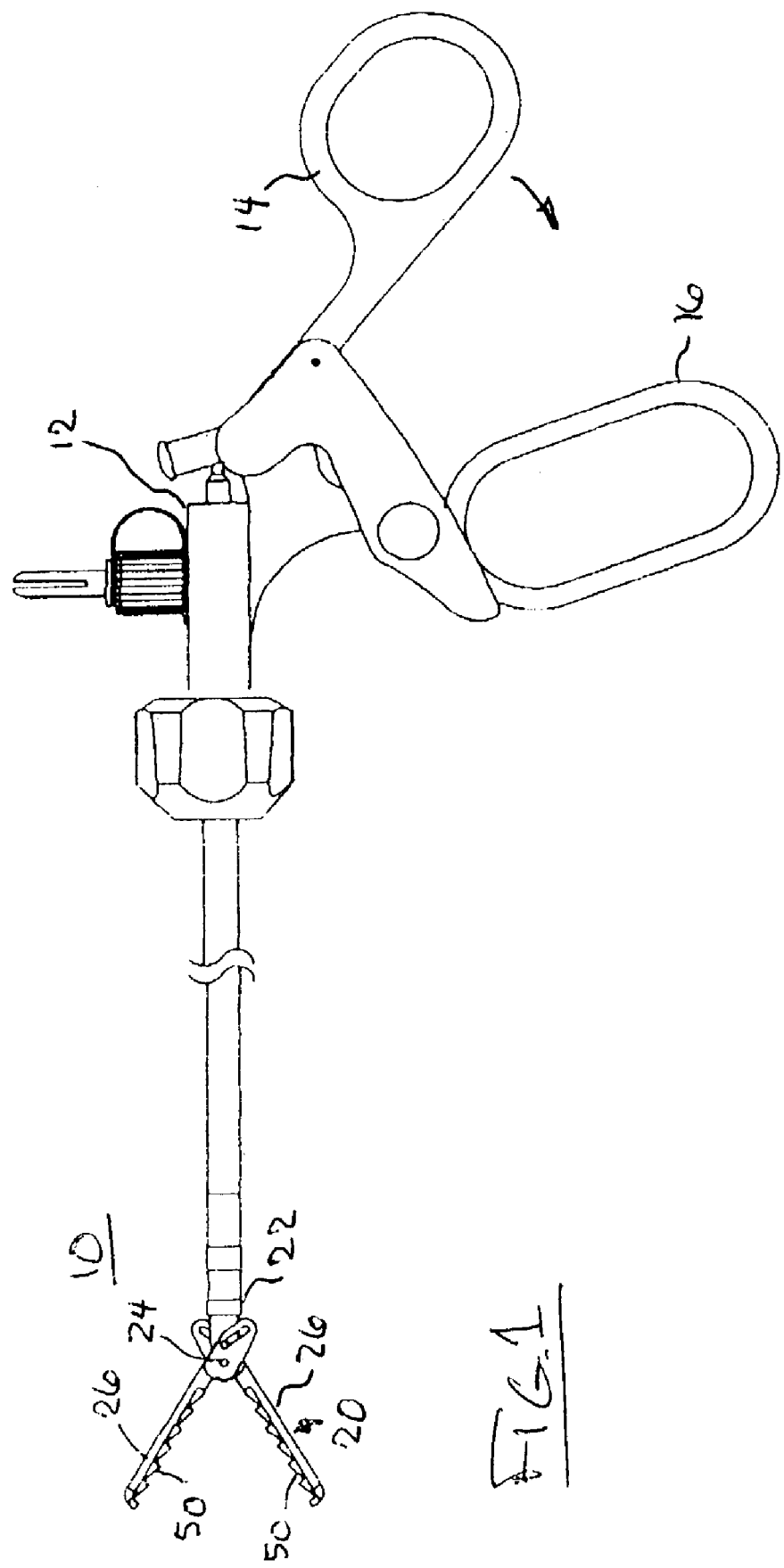
FIG. 1 is a side elevational view of a grasper assembly with a jaw arrangement of the present invention.

The present invention comprises an elongated forceps arrangement or grasper apparatus 10, as shown in FIG. 1, for gently holding and gently manipulating tissue within the human body. The grasper arrangement 10 comprises a first or handle end 12 having a manipulable and squeezable trigger member 14 which is advanceable towards a stationary frame member 16 which actuates a pair of jaws 20 which are located at the second or distal end 22 of the grasper apparatus 10. The jaws 20 at the distal end 22 of the grasper apparatus 10 are arranged to pivot about a pivot pin 24 when the trigger 14 and frame 16 are moved with respect to one another, thus bringing the pair of jaws 20 into engagement or spreading them apart, accordingly.

Figure 2:
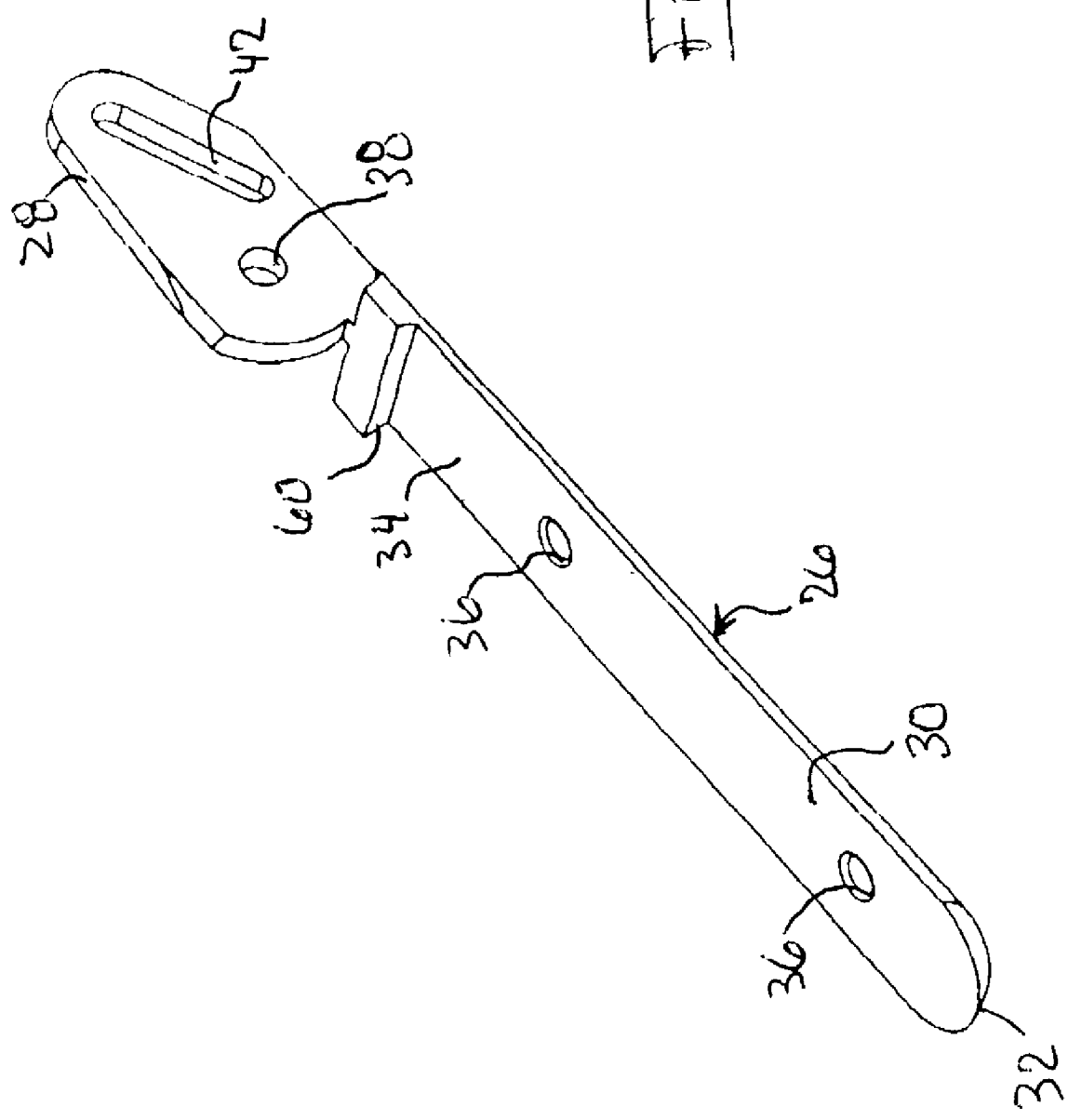
FIG. 2 is a perspective view of an elongated jaw member utilized with the present invention.

Each jaw 26 of the pair of jaws 20 comprises a first end plate 28 of planar configuration which is unitary with an elongated jaw member body 30, as shown in FIG. 2. The elongated jaw member body 30 is generally planar and has a second or distalmost end 32. The elongated jaw member 30 body has a jaw face 34 which is generally flat. The jaw face 34 has a plurality of openings or detents 36 therein. The first end plate 28 has an opening 38 for the pivot pin 24 to extend therethrough, as shown in FIGS. 1, 3, 4 and 5, and has an elongated slot 42 to function as cam slot for the push-pull rod 44, shown in FIG. 5, extending through the housing from the frame 12 at the proximal end of the grasper assembly 10.

Each jaw member 26 is arranged to attachably receive a "grasping-teeth set" 50. Each grasping-teeth set 50 is molded from a soft pliable material such as plastic, polyethylene, polypropylene, rubber or the like. Each grasping-teeth set 50 may have a varying hardness or durometer at its raised portions thereon.

Figure 6:
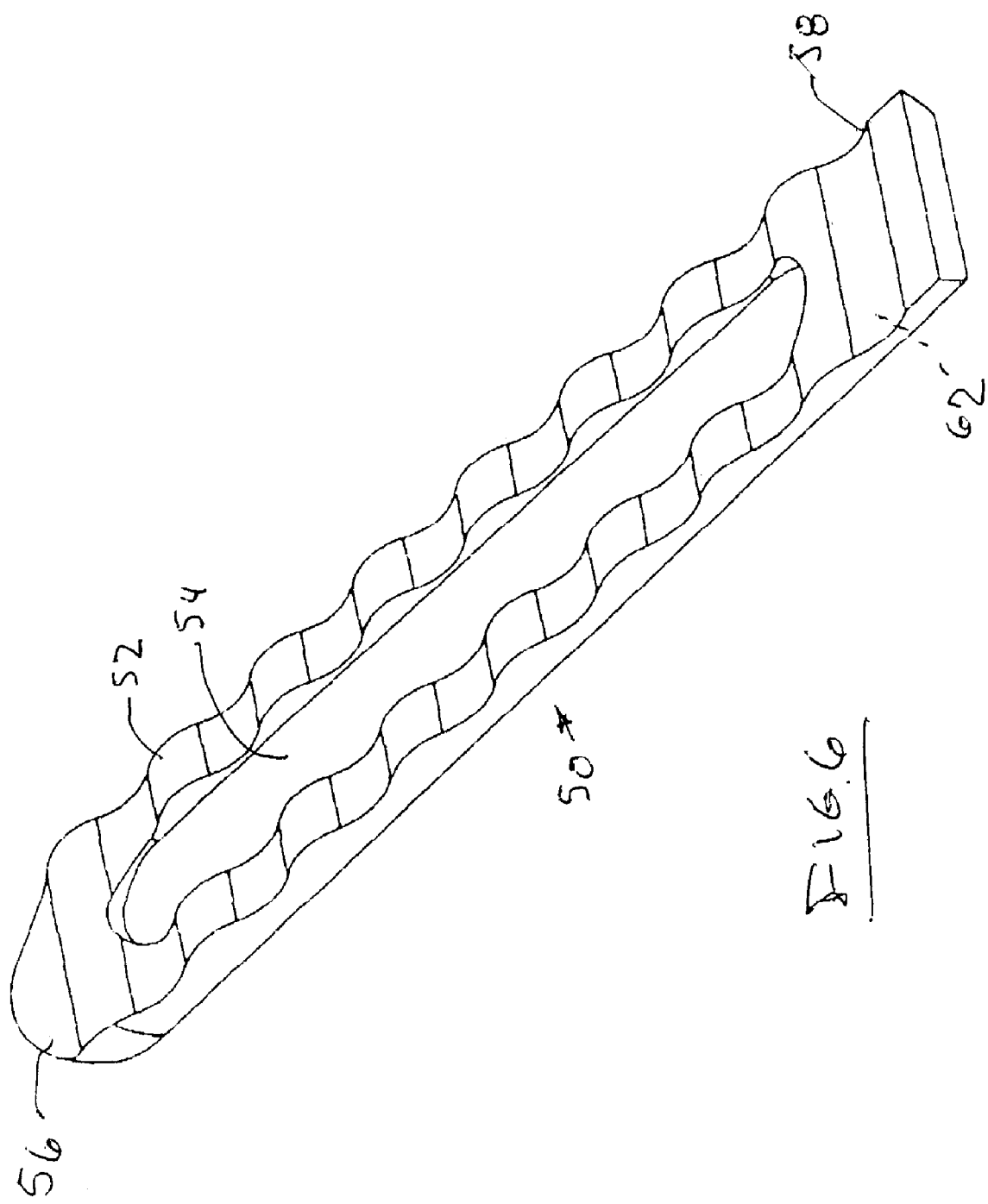
FIG. 6 is a perspective view a first embodiment of the jaw insert of the present invention.
Figure 8:
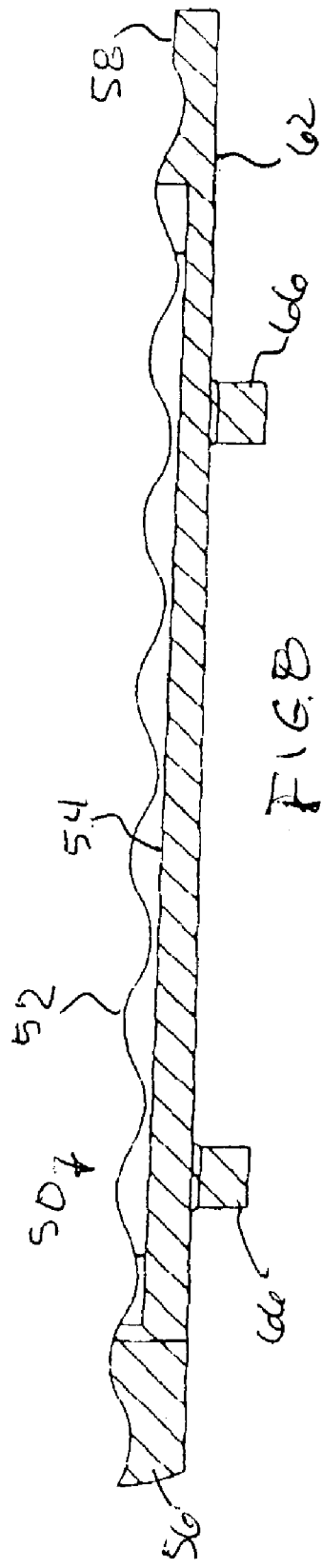
FIG. 8 is a view taken along the lines 8—8 of FIG. 7.
Figure 7:
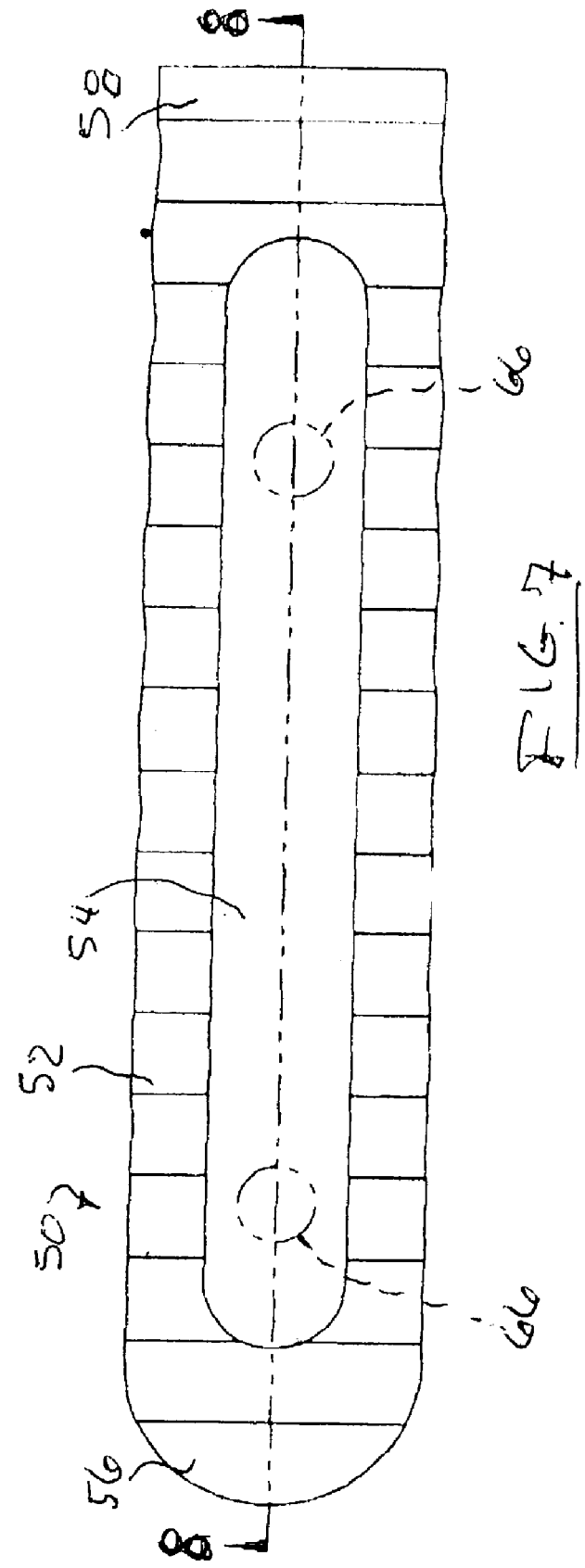
FIG. 7 is a planned view of the jaw insert shown in FIG. 6.

A first embodiment of a grasping-teeth set jaw insert 50 is shown in FIG. 6, which comprises an elongated mold of resilient material which mates with the jaw face 34 of each particular jaw member 26, as represented in FIG. 2. The grasping-teeth set jaw insert 50 in a first preferred embodiment comprises a pair of sinusoidally faced wavy teeth arrays 52, as shown in FIG. 6, and shown assembled in FIGS. 4, 5, 7 and 8, the teeth arrays 52 being spaced apart and parallel, extending along each side edge of the grasping-teeth set jaw insert 50, as best represented in FIG. 6. A central elongated tissue receiving depression or channel 54 is arranged between the respective parallel sinusoidally faced wavy teeth array 52 of this grasping-teeth set jaw insert 50. The wavy faced jaw insert 52 has a distalmost end 56 of curved configuration, which matches the distal end 32 of the jaw face 34 of the elongated jaw member 26 shown in FIG. 2. The grasping-teeth set jaw insert 50 has a proximal end 58 of rectilinear configuration which abuts a placement shoulder 60 at the proximal end of the jaw face 34 of the elongated jaw member 26. The wavy faced (or sinusoidal) grasping-teeth set jaw insert 52 has a back plane 62 which mates against the jaw face 34. A tab 66 extends perpendicular to the back plane 62 of the jaw insert 50 and mates within the openings 36 within the jaw face 34 of its respective elongated jaw member 26. The respective tabs 66 and insert openings 36 snap fit so as to securely mate the grasping-teeth set jaw insert 50 against the particular elongated jaw member 26. Each set of waves 52 in the wavy or sinusoidal tooth array 52 has its crest height diminishing from distal 56 to the proximal end 58 of the jaw insert 50, as may be best seen in FIG. 4. The jaw body 30, in one preferred embodiment, tapers from a thicker distalmost end to a thinner dimension at its proximalmost end, as is best represented in FIG. 8, although that jaw body 30 may also be of constant thickness in other embodiments. The decreasing thickness from distal to proximal ends of the jaw body 30 however, permits a superior distal grasping and gripping of tissue when it is pinched between the pairs of jaws 26 when in use in a body tissue procedure. The elongated tissue receiving channel 54 between the parallel array of wavy teeth 52 in the grasping-teeth set jaw insert 50 also permits body tissue to be safely enclosed therewithin, with minimal damage thereto.

Figure 3:
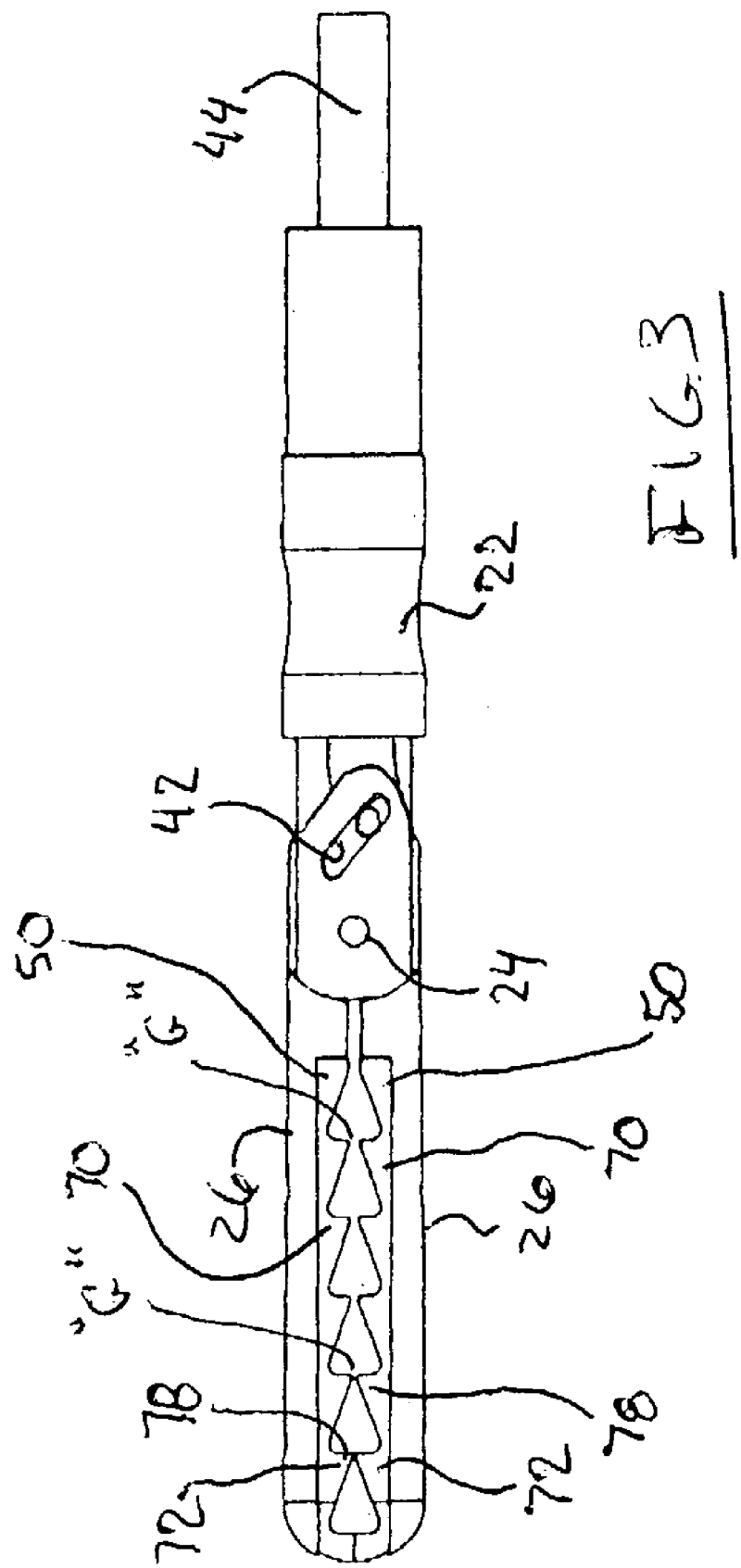
FIG. 3 is a side elevational view of the jaw assembly of the present invention with a saw tooth set of jaw inserts therewith.
Figure 4:
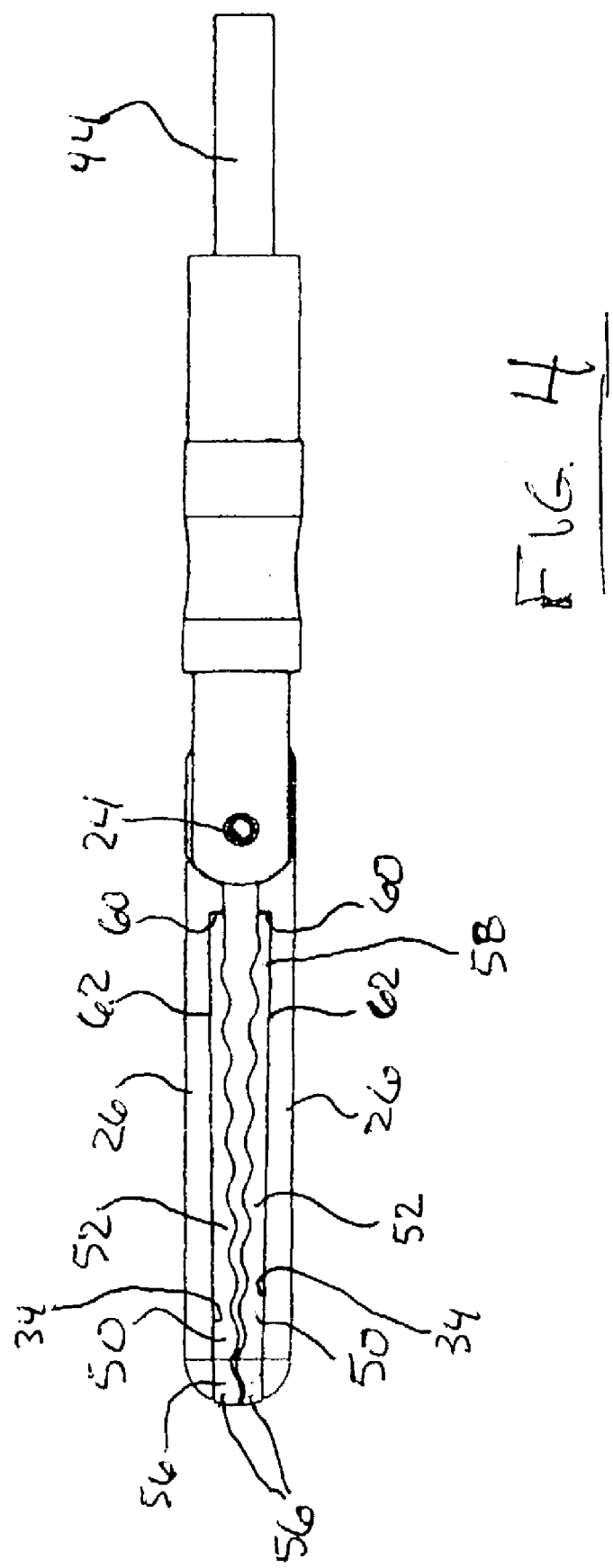
FIG. 4 is a view similar to FIG. 3 with a wavy faced tooth set of inserts secured to the jaw members of the present invention.
Figure 5:
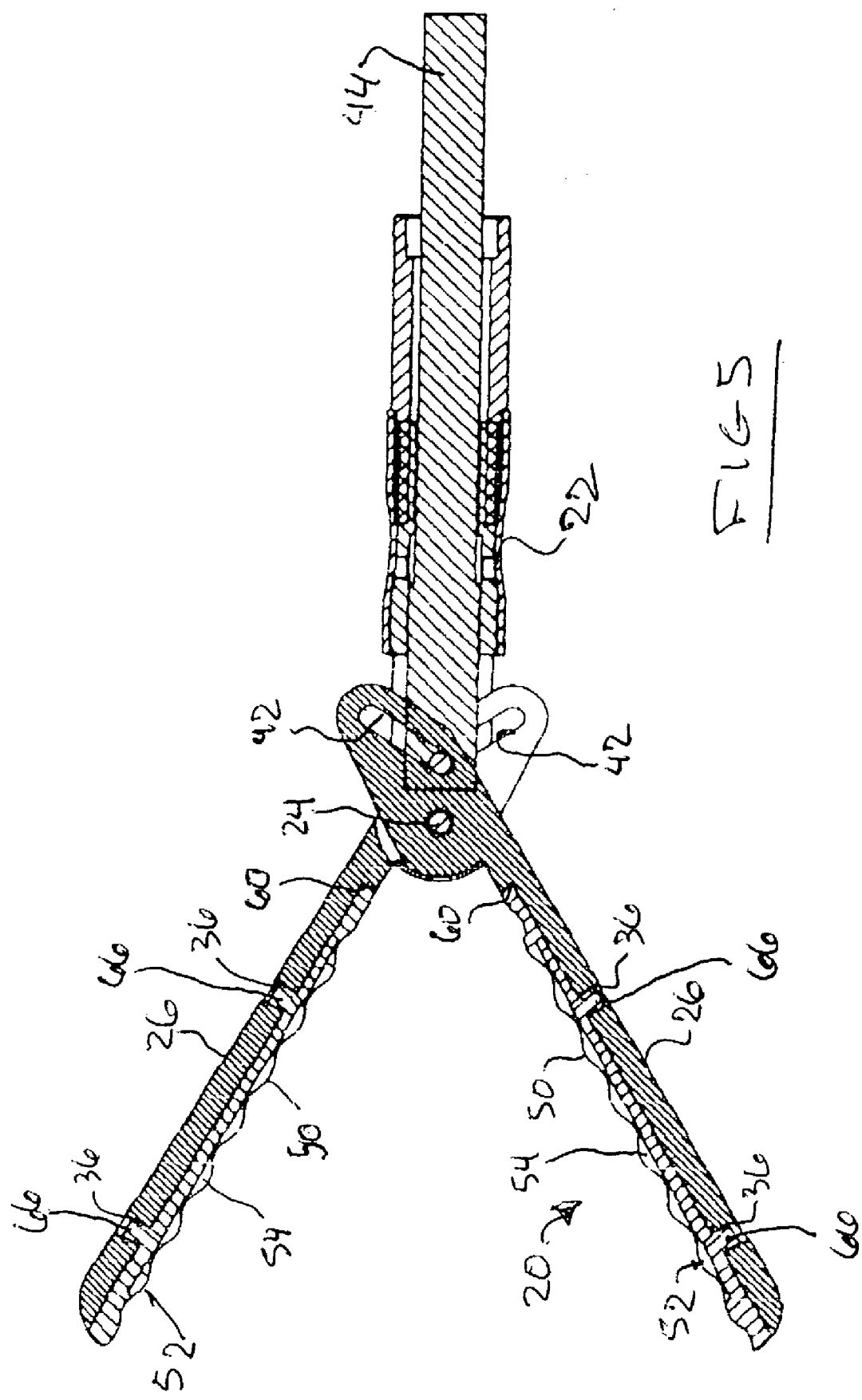
FIG. 5 is side elevational view in section showing the jaw members and jaw inserts of one embodiment of the present invention.

A yet further embodiment of the grasping-teeth set jaw insert 50 comprises an elongated saw-tooth insert 70 having a curved distalmost end 72 and a rectilinear shaped proximal end 74, as shown in FIGS. 9, 10 and 11. There are a series of transversely extending teeth 76 having a "saw tooth" configuration, as best shown in FIGS. 9 and 11. The height of each saw tooth 78 as measured from a back plane 82 of the jaw insert 50 diminishes from the distal end 72 to the proximal end 74 of the jaw insert 50. This permits the saw tooth grasping-teeth set jaw inserts 70, when arranged in a set of elongated jaw members 26, to be in an opposed, abutting relationship when those jaw members 26 are closed. A slightly increasing gap "G" between those opposed teeth 78 of the saw tooth insert 72 is arranged in a proximal direction thereof, which distal to proximal gap "G" increases as best represented in FIG. 3. The side portions of the saw tooth insert 70 have a series of pinched side portions 75 between adjacent teeth 78 to permit a slight flexing of those teeth. The saw tooth configured insert 72 has a plurality of tabs 80 extending perpendicular to its rear planar face. Those tabs 80 are mateably received within the insert openings 36 in the elongated jaw member 26 to permit securement thereto. Adhesive or other fastening means may be utilized on other securement embodiments.

Thus what has been shown is a unique and easily adaptable arrangement of attachable jaw members 50 to permits a patient's tissue to be safely grasped by the operating surgeon.

We claim:

1. A grasper arrangement having a pair of opposed, elongated, movable jaw members at a distal end of said grasper arrangement pinchably actuatable from a handle portion at a proximal end of said grasper arrangement, said jaw members each having a toothed insert attachably secured thereon to thus comprise a pair of opposed toothed inserts;

each said toothed insert having an array of teeth disposed on a first side thereof to grasp body tissue therewith, wherein said array of teeth has a wavy sinusoidal shape when viewed from a longitudinal cross section of each said toothed insert, and wherein a crest height of said array of teeth decreases from a distal end of the movable jaw members toward a proximal end of the movable jaw members so as to form a gradually increasing gap therebetween, and said gap increases towards the proximal end of the movable jaw members and each said toothed insert having a securement on a second side thereof to securely engage said jaw members thereto.

2. The grasper arrangement as recited in claim 1, wherein each of said jaw members are of decreasing tapered thickness from a distal end thereof to a proximal end thereof to improve pinching of tissue.

3. The grasper arrangement as recited in claim 1, wherein each said toothed insert is of decreasing thickness from a distal end thereof to a proximal end thereof to improve pinching of tissue.

4. The grasper arrangement as recited in claim 1, wherein said array of teeth has an elongated channel formed parallel to bottom surfaces of at least one of said toothed inserts, and extending longitudinally from a distal end to a proximal end of at least one of said toothed inserts.

5. The grasper arrangement as recited in claim 1, wherein said securement comprises a tab extending off of a backside of each of said tooth inserts to mate with said jaw members.

6. The grasper arrangement as recited in claim 1, wherein said securement comprises an adhesive disposed between each said toothed insert and said jaw members.

7. The grasper arrangement as recited in claim 5, wherein each of said jaw members has an indentation to receive said tab on said tooth insert.

8. The grasper arrangement as recited in claim 1, wherein said toothed inserts are comprised of soft resilient material.

9. The grasper arrangement as recited in claim 1, wherein the jaw members each have a first end plate provided with an elongated slot that operates as a cam slot with a push pull rod at a proximal end of the grasper arrangement.

* * * * *